(12) United States Patent
Bittner

(10) Patent No.: US 7,408,352 B2
(45) Date of Patent: Aug. 5, 2008

(54) MAGNETIC RESONANCE UNIT

(75) Inventor: Gerhard Bittner, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/709,660

(22) Filed: Feb. 22, 2007

(65) Prior Publication Data

US 2007/0210797 A1  Sep. 13, 2007

(30) Foreign Application Priority Data

Feb. 24, 2006 (DE) ................ 10 2006 008 724

(51) Int. Cl.
*G01V 3/00* (2006.01)
(52) U.S. Cl. ...................... 324/318; 324/322
(58) Field of Classification Search ................ 324/318, 324/322; 600/415
See application file for complete search history.

(56) References Cited

U.S. PATENT DOCUMENTS

| 4,634,980 | A | * | 1/1987 | Misic et al. ................ 324/322 |
| 4,972,852 | A | * | 11/1990 | Koob et al. ................ 600/415 |
| 5,197,474 | A | * | 3/1993 | Englund et al. ............ 600/415 |
| 7,071,692 | B2 | * | 7/2006 | Branch et al. .............. 324/318 |

FOREIGN PATENT DOCUMENTS

| DE | 103 34 326 A1 | 2/2005 |
| DE | 10 2004 042 100 A1 | 1/2006 |

\* cited by examiner

*Primary Examiner*—Louis M Arana

(57) ABSTRACT

The invention relates to a magnetic resonance unit, with a magnet generating a static magnetic field, in the hollow space of which an essentially tubular inner lining is disposed, into which a patient support device can be introduced, and with control elements disposed on a front lining to control the magnetic resonance unit. It is possible to introduce the patient support device and the inner lining, which surrounds the patient support device and can be moved in relation to the patient support device, into the hollow space of the magnet and to remove them therefrom together.

15 Claims, 5 Drawing Sheets

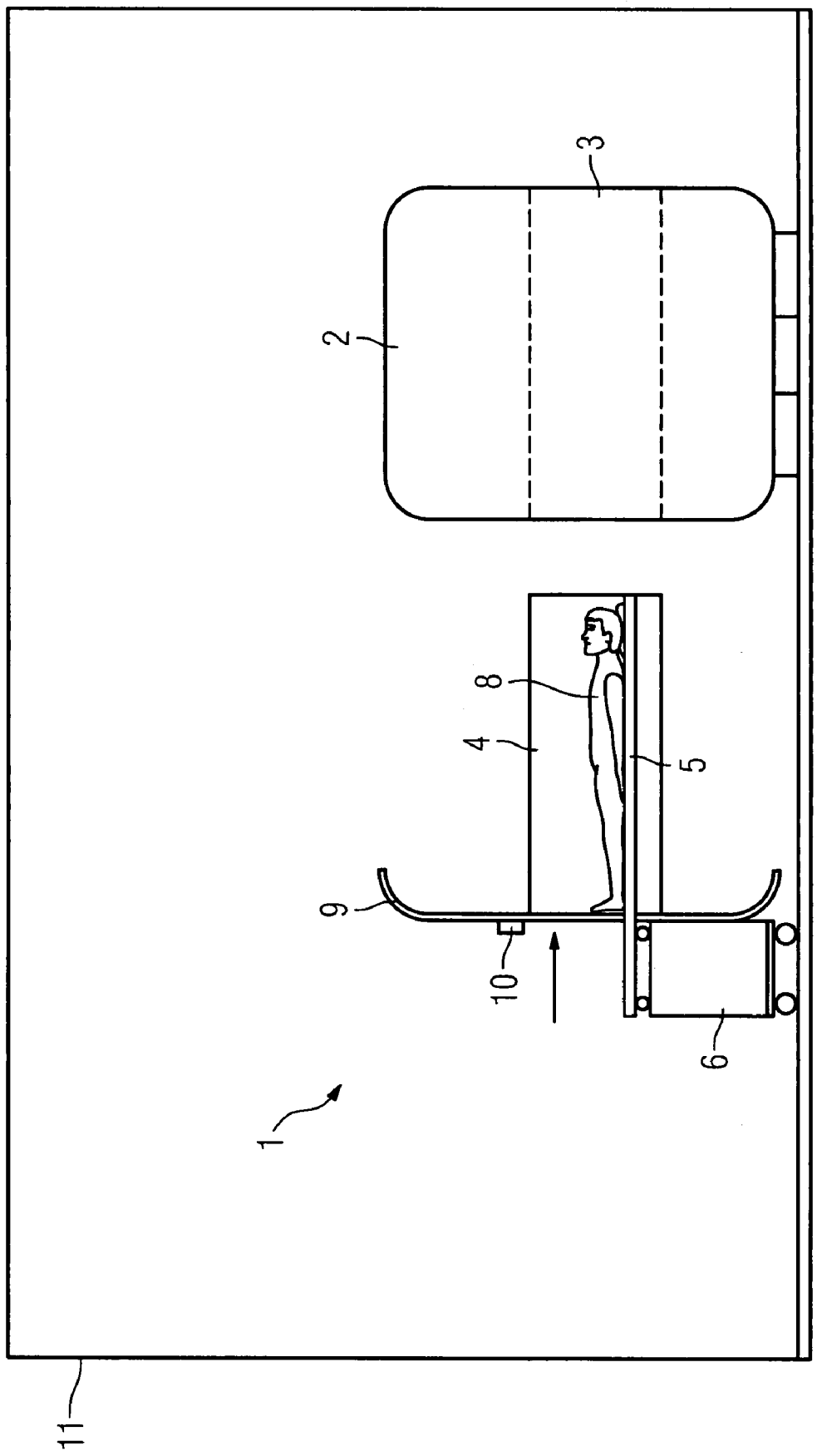

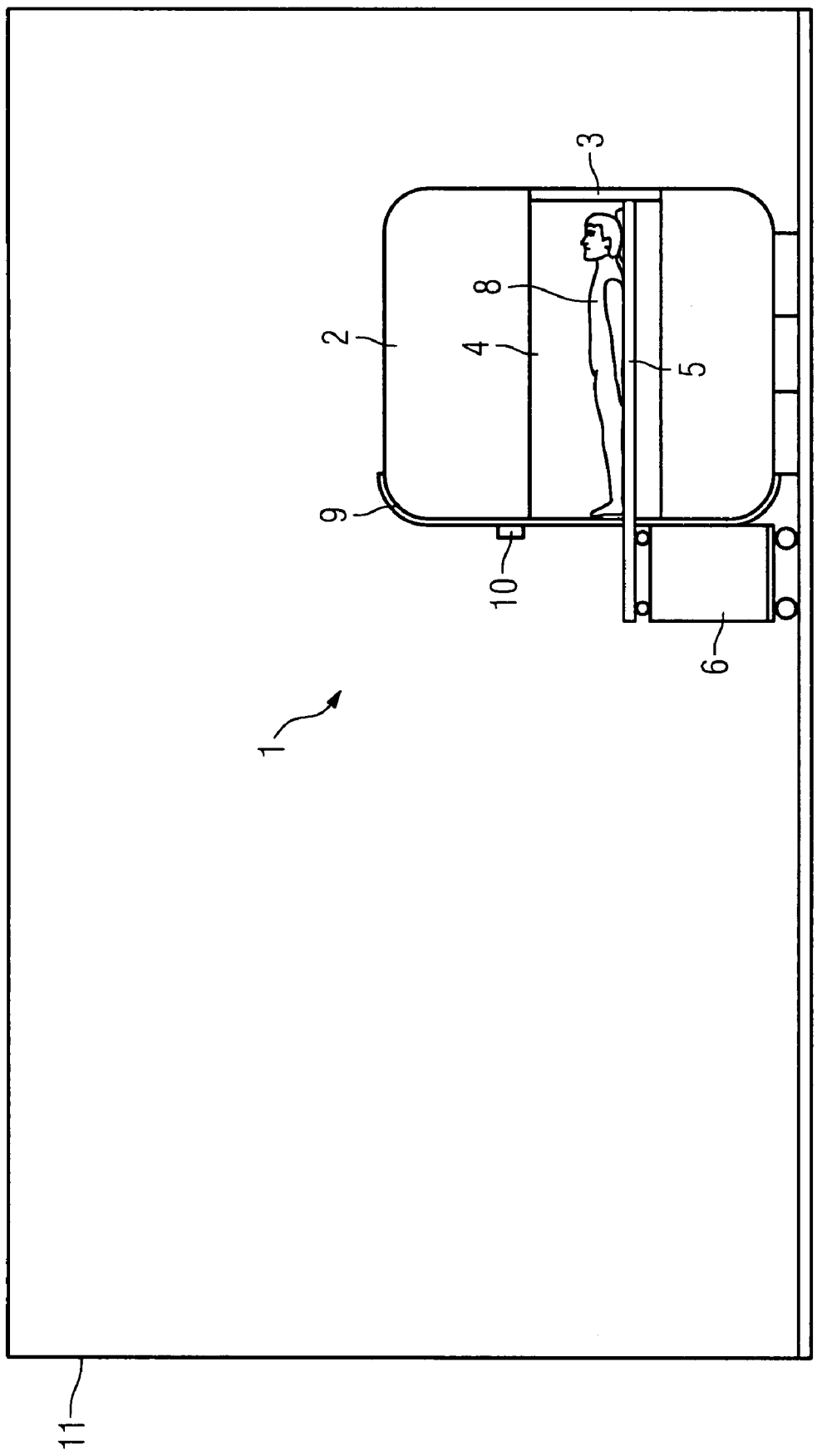

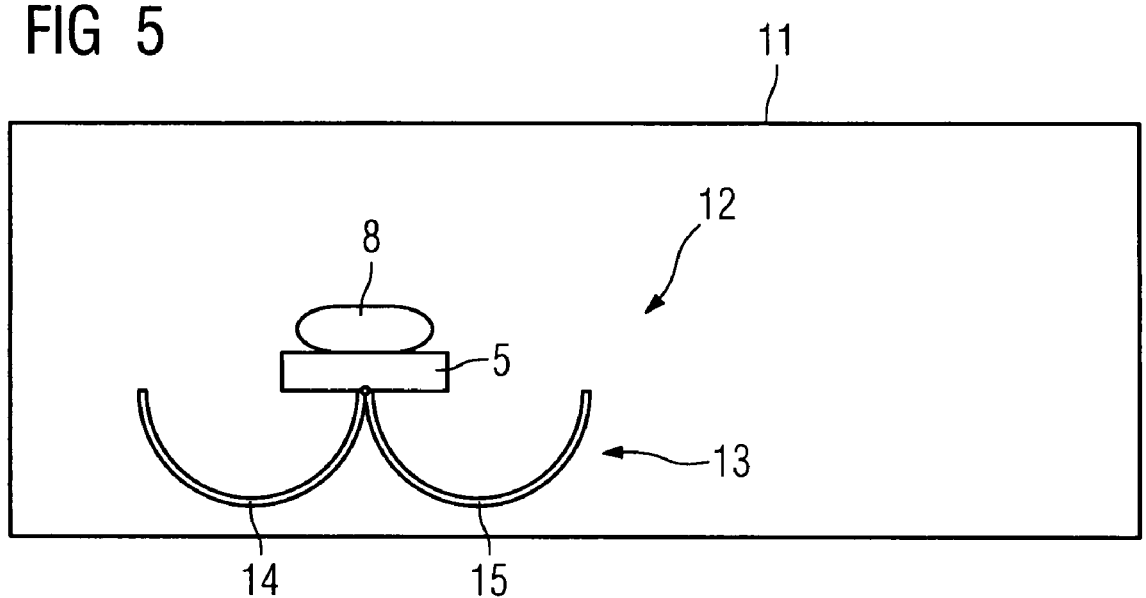
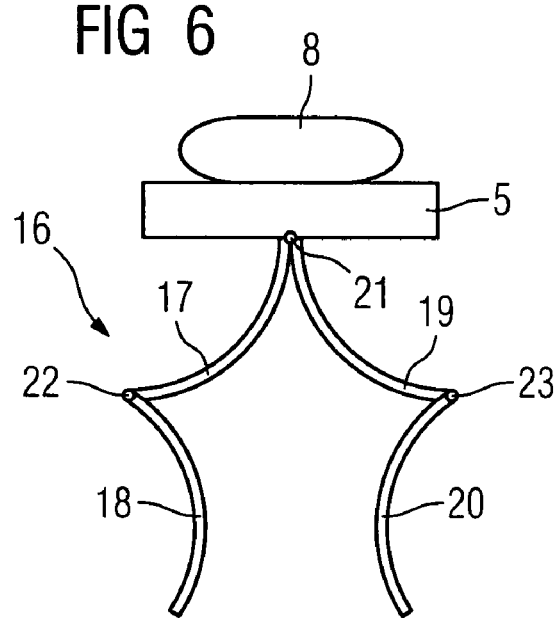
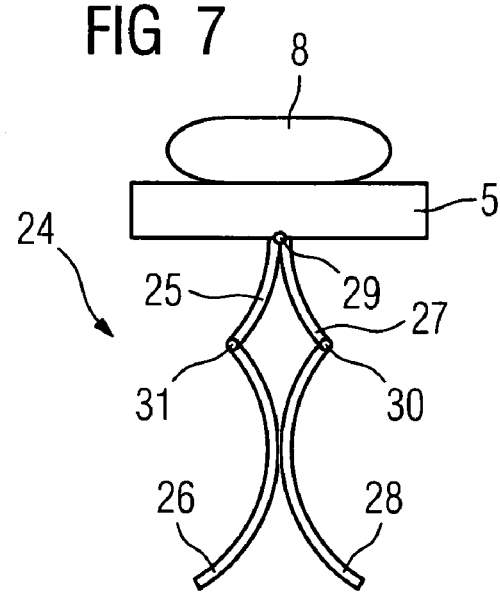

MAGNETIC RESONANCE UNIT

CROSS REFERENCE TO RELATED APPLICATIONS

This application claims priority of German application No. 10 2006 008 724.0 filed Feb. 24, 2006, which is incorporated by reference herein in its entirety.

FIELD OF THE INVENTION

The invention relates to a magnetic resonance unit with a magnet generating a static magnetic field, in the hollow space of which magnet an essentially tubular inner lining is disposed, into which a patient support device can be introduced, and with control elements disposed on the front lining to control the magnetic resonance unit.

BACKGROUND OF THE INVENTION

With conventional magnetic resonance units it is unavoidable that the operators regularly stand in very close proximity to the magnet of the magnetic resonance unit, to position the patient on the patient support device, which can for example be configured as a patient bed or to help said patient leave. The patient bed is usually designed such that it can only be moved as far as is absolutely necessary out of the hollow space of the magnet. Also control elements such as switches, a keypad and in some instances also corresponding output elements, such as a display unit, can also be disposed on the outside of the magnetic resonance unit, so that the operators generally have to stand for quite a long time in direct proximity to the magnet, to adjust or control the magnetic resonance unit.

Although according to current knowledge of magnetic resonance units they do not represent a hazard, there has recently been some discussion among elements of the public, whether the presence of people in electromagnetic fields is associated with an adverse effect on their health. Static magnetic fields, as are present in the area around a conventional magnetic resonance unit, are deemed to be problematic, as well as electromagnetic alternating fields. The operators of a magnetic resonance unit have to stand in very close proximity to the magnet when introducing a patient into the hollow space of the magnet and positioning them there, with the result that they spend quite a long time in static magnetic fields. At the same time there is a tendency to use increasingly strong magnetic fields for MR imaging. New MR systems, that are currently available, operate with a magnetic flux density of 2 tesla, while in the near future magnetic resonance units will operate at 3 tesla and for research purposes units operating at 7 to 10 tesla are already being designed and developed, with the result that the problems mentioned will take on an even greater significance.

Until now the patient support device, in particular the patient bed, has been designed in such a manner that it is located in proximity to the magnet. If it were to move out further, a larger high-frequency cabin would be required for the magnetic resonance unit. Conventional magnetic resonance units however have the disadvantage that the operators have to ensure, during introduction into the hollow space of the magnet, that lines, hoses, etc. do not become trapped between the patient bed and the inner lining. As mentioned above, the control elements required to move the patient bed in and out are normally attached to the front lining of the magnetic resonance unit, in such a manner that the operators are permanently in the area of influence of the static magnetic field during the entire procedure of positioning the patient for introduction into the hollow space.

SUMMARY OF THE INVENTION

The object of the invention is therefore to create a magnetic resonance unit, with which the operators are exposed to a less significant degree to the influence of static magnetic fields.

To achieve this object, with a magnetic resonance unit of the type mentioned above provision is made according to the invention for the patient support device and the inner lining, which surrounds it and can be moved in relation to it, to be able to be introduced into the hollow space of the magnet and be removed therefrom together.

The invention is based on the knowledge that the procedures "positioning the patient on the patient support device" and "introducing the patient support device with the patient into the magnet" can be separated spatially, in such a manner that the operators do not have to step directly up to the magnet. According to the invention provision is made for the patient support device and the inner lining of the magnet to be able to be moved into the hollow space of the magnet and out again together. To this end the patient support device is moved out from the hollow space of the magnet together with the inner lining, in which state the patient can be positioned on the patient support device at a relatively large distance from the magnet. The patient support device is then moved into the hollow space of the magnet together with the inner lining. During this entire procedure it is not necessary for the operators to stand in direct proximity to the magnet.

According to a development of the invention provision can be made for the patient support device and the inner lining surrounding it to be able to be moved together with a lining of the magnet that has control elements. If the lining, in particular the front lining, of the magnet can be moved out together with the patient support device and the inner lining, all the control procedures can be carried out at a distance from the magnet.

Further facilitation is achieved in that the patient support device of the inventive magnetic resonance unit and/or the inner lining can be moved relative to the other element to support the patient. This can be achieved in that the patient support device can be moved out of the inner lining; alternatively the inner lining can be moved away from the patient support device. In both instance the patient support device, for instance a patient bed, is freely accessible, such that the patient can easily be moved into the required position for the magnetic resonance examination. These procedures take place in a position, where the static magnetic field is significantly weaker than it is directly in front of the magnet.

A particularly simple structure of the inventive magnetic resonance unit results, when the patient support device and/or the inner lining can be displaced by way of linear movements, preferably by means of electric motors.

The unit, comprising the inner lining and the patient support device, which is separate from the actual magnetic resonance unit and the magnet, contains motors and other modules, which on the one hand have to be supplied with energy, while on the other hand they have to communicate with the other components of the magnetic resonance unit. The energy can thereby be supplied electrically and in some instances also pneumatically or hydraulically. The connections for supplying the necessary energy can be configured as plug connections or cables or lines, in the case of electrical, pneumatic and hydraulic energy. Communication between the individual modules can take place by way of electrical lines, plug connections, radio connections, optical waveguides or by way of optical transmission links.

In an alternative embodiment of the inventive magnetic resonance unit provision can be made for the inner lining to have two half shells, which can be folded out to support the patient and in the closed state form the tubular inner lining. With this variant the patient can easily be positioned on the patient support device in the folded out state. The operators can then check that the cables to surface coils are lying correctly, the arms and legs of the patient are correctly positioned and no parts of the body are up against or being squashed by the inner lining. This procedure takes place a long way away from the magnet. The inner lining, which comprises two half shells, can be structured in such a manner that in the folded out state the two half shells are disposed next to each other above or below the patient support device. Both instances provide good accessibility to the patient support device and therefore to the patient.

To increase accessibility further with the inventive magnetic resonance unit, provision can be made for each half shell to comprise a number of, preferably two, shell segments, which are connected together by means of an articulation. The shell segments can be folded down at the articulation, in such a manner that the shell segments do not obstruct in a disruptive manner. A further improvement can be achieved in that the outer shell segments are longer than the inner shell segments disposed on the patient support device. The shell segments can thereby be folded or swung practically completely below the patient support device, thereby providing optimum access to the patient.

The inventive magnetic resonance unit is preferably disposed within a high-frequency screening cabin, which can be configured to be a little larger than conventional screening cabins.

BRIEF DESCRIPTION OF THE DRAWINGS

Further advantages and details of the invention are described based on exemplary embodiments with reference to the figures, which are schematic diagrams, in which:

FIG. 3 shows the magnetic resonance unit after the introduction of the patient support device into the inner lining;

FIG. 4 shows the inventive magnetic resonance unit after the introduction of the patient support device and the inner lining into the hollow space of the magnet;

FIG. 5 shows a second exemplary embodiment of the inventive magnetic resonance unit;

FIG. 6 shows a third exemplary embodiment of the inventive magnetic resonance unit; and FIG. 7 shows a fourth exemplary embodiment of the inventive magnetic resonance unit.

DETAILED DESCRIPTION OF THE INVENTION

Figure 1:
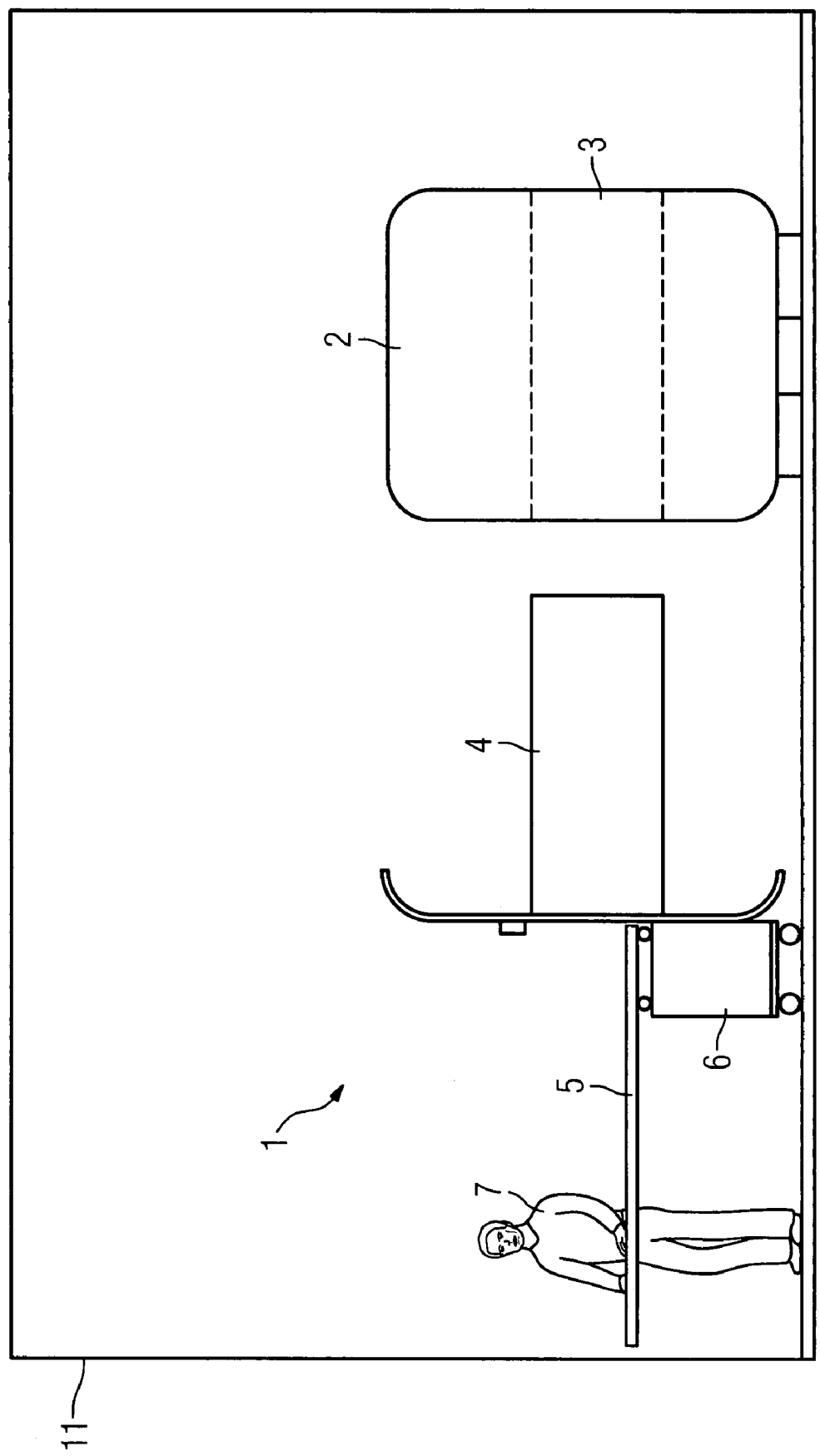
FIG. 1 shows an inventive magnetic resonance unit.

The magnetic resonance unit 1 shown in FIG. 1 comprises a magnet 2, which is configured in a tubular shape, and a cylindrical hollow space 3. The magnet coils of the magnet 2 generate a not insignificant static magnetic field.

The magnetic resonance unit 1 also comprises an inner lining 4, the diameter and length of which are tailored to the hollow space 3 of the magnet 2. Means not shown in detail in FIG. 1, such as electric motors, can be used to introduce the inner lining 4 by way of a linear movement into the hollow space 3 of the magnet 2 and take it out again. The inner lining 4 is connected to a patient support device configured as a patient bed 5, which is supported and moved on a moving device body 6.

As shown schematically in FIG. 1, the patient bed 5 can be moved and displaced relative to the device body 6, to move the patient bed 5 into the inner lining 4 and back out again. When a patient is to be positioned on the patient bed 5, an operator 7 is located a long way away from the magnet 2, so that the influence of the static magnetic fields on the operator 7 is negligibly small.

Figure 2:
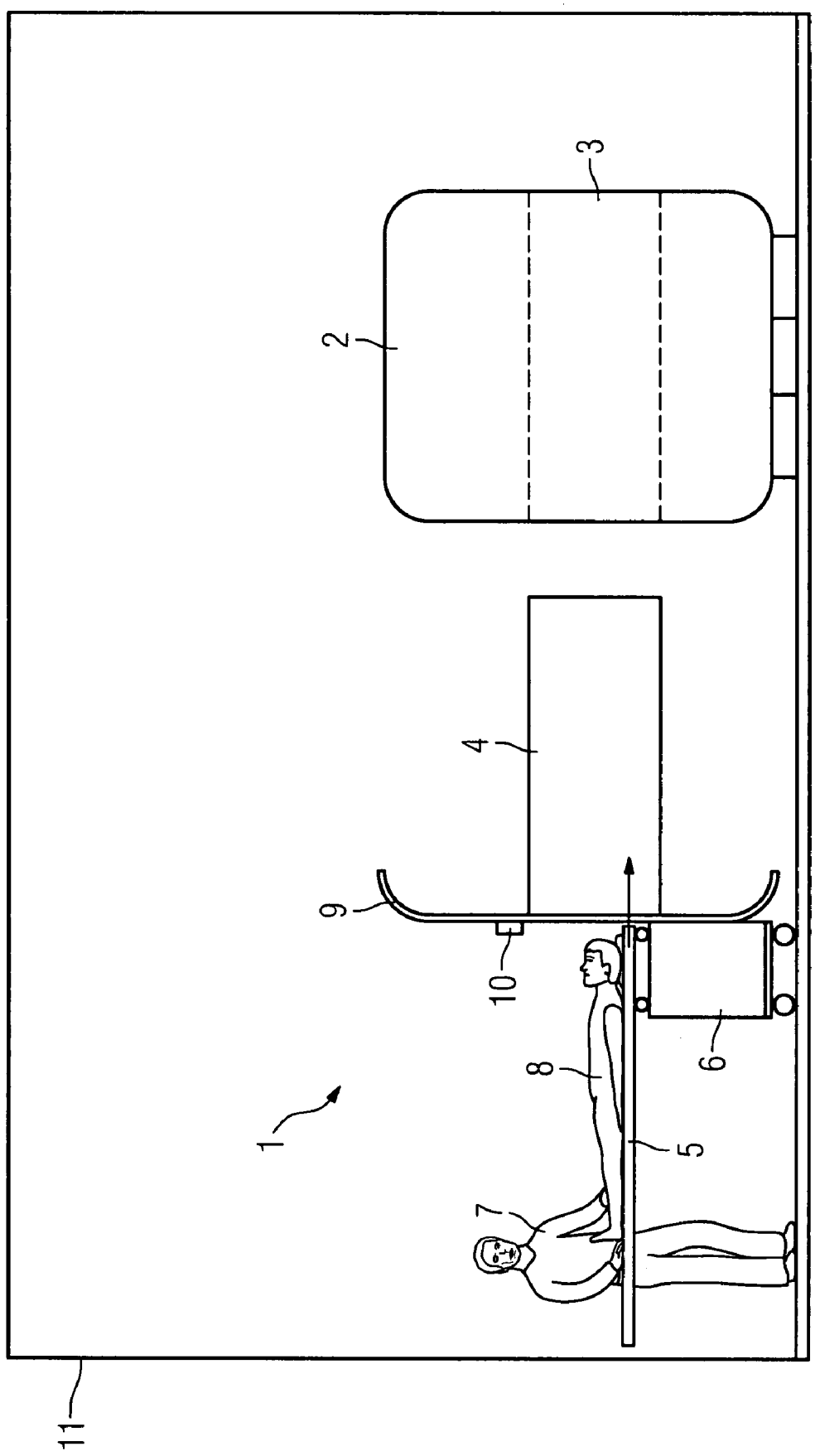
FIG. 2 shows the magnetic resonance unit from FIG. 1 with a patient.

FIG. 2 shows the magnetic resonance unit 1, after a patient 8 has been positioned and supported on the patient bed 5. The operator can position the hands, feet, etc. of the patient 8 in an appropriate manner for the intended magnetic resonance examination, which presents no problem given the very good accessibility of the patient 8.

At the front of the inner lining 4 is a front lining 9, which is in turn connected to the device body 6. Control elements 10 (only shown schematically) are located on the front lining 9 and these are used to control the movement of the patient bed 5 into and out of the inner lining 4. As shown in FIG. 2, the entire magnetic resonance unit is located within a high-frequency screening cabin 11.

FIG. 3 shows the magnetic resonance unit 1 after the introduction of the patient bed 5, on which the patient 8 is supported, into the inner lining 4. This introduction procedure is controlled by the operator by way of the control elements 10 located on the front lining 9. It is checked beforehand that no hoses, cables, etc. are causing a disruptive obstruction, as they might otherwise become trapped during the introduction procedure. As shown in FIG. 3, the patient 8 is located completely within the inner lining 4.

FIG. 4 shows the magnetic resonance unit 1, after the inner lining 4 together with the base body 6 and front lining 9 has been moved up to the magnet 2, in such a manner that the inner lining 4 is located in the hollow space 3 of the magnet 2. This introduction procedure is similarly initiated by the operator by way of the control elements 10 on the front lining 9. The magnetic resonance examination can be carried out in the state shown in FIG. 4. After the examination has been completed, the inner lining 4 together with the patient bed 5, the front lining 9 and the device body 6 is moved back into the position shown in FIG. 3, after which the patient bed 5 is moved out from the inner lining 4, in such a manner that the state shown in FIG. 2 results. The patient 8 can then leave the patient bed 5.

FIG. 5 shows a schematic diagram of a second exemplary embodiment of a magnetic resonance unit 12, wherein the inner lining 13, in contrast to the one in the first exemplary embodiment, is made up of two half shells 14, 15, which can be folded out to support the patient and form a tubular inner lining in the closed state. In the folded out state the half shells 14, 15 provide particularly good accessibility to the patient bed 5 and to the patient 8. The half shells 14, 15 are attached below the patient bed 5 and can be swung into the closed position about this fixing point. The entire arrangement, comprising the inner lining 13 and patient bed 5, is then moved together into the hollow space of the magnet.

FIG. 6 shows a third exemplary embodiment of a magnetic resonance unit 16 as a development of the magnetic resonance unit shown in FIG. 5. In the exemplary embodiment shown in FIG. 6 the two half shells, which form the inner lining in the closed state, comprise four shell segments 17-20, with the shell segments 17, 19 being fixed in an articulated manner to a first articulation 21 below the patient bed 5. At the other end of the shell segments 17, 19 in each instance are second articulations 22, 23, such that the outer or lower shell segments 18, 20 can be folded below the patient bed 5, in such a manner that the patient bed 5 and therefore the patient 8 are particularly easily accessible. The shell segments 17-20 are folded or swung down by way of electric motors (not shown) or manually.

FIG. 7 shows a fourth exemplary embodiment of a magnetic resonance unit 24, wherein, as in the exemplary embodiment shown in FIG. 6, four shell segments 25-28 are provided, with the upper shell segments 25, 27 being fixed in an articulated manner to an upper articulation 29 and the lower shell segments 26, 28 being connected by way of articulations 30, 31 to the upper shell segments 25, 27. Since the upper shell segments 25, 27 are significantly shorter than the lower shell segments 26, 28, all the shell segments 25-28 can be swung completely below the patient bed 5, as shown in FIG. 7, in such a manner that the shell segments 25-28 do not cause a disruptive obstruction when the patient 8 is supported. The structure shown in FIG. 7 ensures optimum accessibility.

The invention claimed is:

1. A magnetic resonance unit for performing a medical procedure, comprising:
   a magnet that generates a static magnetic field;
   an essentially tubular inner lining that is disposed in a hollow space of the magnet;
   a patient support device that can be introduced into the inner lining and further introduced into and removed from the hollow space of the magnet together with the inner lining; and
   a control element that is disposed on a front lining of the inner lining to control a movement of the patient support device and the inner lining.

2. The magnetic resonance unit as claimed in claim 1, wherein the patient support device is surrounded by the inner lining.

3. The magnetic resonance unit as claimed in claim 1, wherein the patient support device and the inner lining is moved relative to each other.

4. The magnetic resonance unit as claimed in claim 1, wherein the patient support device or the inner lining is moved with a linear movement.

5. The magnetic resonance unit as claimed in claim 4, wherein the patient support device or the inner lining is moved by an electric motor.

6. The magnetic resonance unit as claimed in claim 1, wherein the inner lining comprises two half shells.

7. The magnetic resonance unit as claimed in claim 6, wherein the half shells are disposed next to each other above or below the patient support device when opened out.

8. The magnetic resonance unit as claimed in claim 6, wherein the half shells form the tubular inner lining when closed.

9. The magnetic resonance unit as claimed in claim 6, wherein each of the half shells comprises a plurality of shell segments that are connected together by an articulation.

10. The magnetic resonance unit as claimed in claim 9, wherein each of the half shells comprises two shell segments.

11. The magnetic resonance unit as claimed in claim 9, wherein the shell segments comprises an outer shell segment and an inner shell segment.

12. The magnetic resonance unit as claimed in claim 11, wherein the outer shell segment is longer than the inner shell segment.

13. The magnetic resonance unit as claimed in claim 1, wherein magnetic resonance unit is disposed within a high-frequency screening cabin.

14. A magnetic resonance unit for performing a medical procedure, comprising:
    a magnet that generates a static magnetic field;
    an inner lining that is disposed in a hollow space of the magnet and has an essentially tubular shape;
    a patient support device that can be introduced into the inner lining and further introduced into and removed from the hollow space of the magnet together with the inner lining;
    a front lining that is at a front of the inner lining; and
    a control element that is disposed on the front lining to control a movement of the inner lining and the patient support device.

15. A method for operating a magnetic resonance unit in a medical procedure, comprising:
    generating a static magnetic field by a magnet;
    disposing a tubular inner lining in a hollow space of the magnet;
    introducing a patient support device into the inner lining and further introducing into and removing from the hollow space of the magnet together with the inner lining;
    arranging a control element at a front lining of the inner lining; and
    controlling a movement of the inner lining and the patient support device by the control element.

* * * * *